United States Patent [19]

Banholzer et al.

[11] Patent Number: 4,699,910

[45] Date of Patent: Oct. 13, 1987

[54] N-(3-TRIFLUOROMETHYL-PHENYL)-N'-PROPARGYL-PIPERAZINE AND SALTS THEREOF USEFUL AS ANALGESICS

[75] Inventors: Rolf Banholzer; Herbert Merz, both of Ingelheim; Klaus Stockhaus, Bingen; Hans M. Jennewein, Walluf, all of Fed. Rep. of Germany

[73] Assignee: Boehringer Ingelheim KG, Ingelheim am Rhein, Fed. Rep. of Germany

[21] Appl. No.: 800,525

[22] Filed: Nov. 22, 1985

Related U.S. Application Data

[63] Continuation of Ser. No. 665,777, Oct. 29, 1984, abandoned, which is a continuation of Ser. No. 581,137, Feb. 17, 1984, abandoned.

[30] Foreign Application Priority Data

Feb. 28, 1983 [DE] Fed. Rep. of Germany ....... 3306964

[51] Int. Cl.$^4$ .................. A61K 31/505; C07D 241/04
[52] U.S. Cl. ..................................... 514/255; 544/385; 544/392; 544/395; 564/305
[58] Field of Search .................. 544/392, 395; 514/255

[56] References Cited

U.S. PATENT DOCUMENTS 2,993,899  7/1961  Dawson et al. ...................... 544/392
3,458,514  7/1969  Palazzo et al. ...................... 544/392

FOREIGN PATENT DOCUMENTS 2800954  7/1978  Fed. Rep. of Germany .
2078746  1/1982  United Kingdom .

OTHER PUBLICATIONS

May & Baker Ltd., Chem. Abst., vol. 67, 43820t.
Centre d'Etudes pour l'Industrie Pharmaceutique, Chem. Abst. 84-164848t.
Banholzer et al, Chem. Abst. 102-62257x.

Primary Examiner—Donald G. Daus
Assistant Examiner—Cecilia Shen
Attorney, Agent, or Firm—Hammond & Littell, Weissenberger & Dippert

[57] ABSTRACT

The compound of the formula

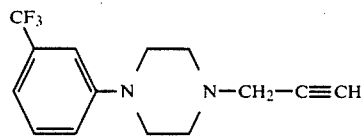

and non-toxic, pharmacologically acceptable acid addition salts thereof. The compound as well as its salts are useful as analgesics.

4 Claims, No Drawings

N-(3-TRIFLUOROMETHYL-PHENYL)-N'-PROPARGYL-PIPERAZINE AND SALTS THEREOF USEFUL AS ANALGESICS

This is a continuation of Ser. No. 665,777, filed Oct. 29, 1984, now abandoned, which is the continuation of Ser. No. 581,137 filed on Feb. 17, 1984, now abandoned.

This invention relates to a novel N-phenyl-piperazine derivative and non-toxic salts thereof, to methods of preparing these compounds, to pharmaceutical compositions containing them as active ingredients, and to methods of using them as analgesics.

More particularly, the present invention relates to the novel compound N-(3-trifluoromethyl-phenyl)-N'-propargylpiperazine represented by the formula

[Structure I: 3-CF₃-phenyl-N(piperazine)N—CH₂—C≡CH]   (I)

and non-toxic, pharmacologically acceptable acid addition salts thereof.

The novel compound of the formula I may be prepared by various methods involving piperazine ring closure, attachment of the propargyl substituent to the piperazine radical or reduction of a corresponding piperazine-dione, of which the following are illustrative:

Method A

Reaction of a compound of the formula

[Structure II: 3-CF₃-phenyl-N(CH₂—CH₂—X)₂]   (II)

in which X represents a group which can easily be split off anionically, such as a halogen atom or an alkyl- or aryl-sulfonyloxy group, with N-propargyl-amine of the formula

HC≡C—CH₂—NH₂   (III)

at temperatures between room temperature and the boiling point of the reaction mixture.

Method B

Reaction of a compound of the formula

HC≡C—CH₂—N(CH₂—CH₂—X)₂   (IV)

in which X has the above-mentioned meanings, with trifluoromethyl aniline of the formula

[Structure V: 3-CF₃-phenyl-NH₂]   (V)

at temperatures between room temperature and the boiling point of the reaction mixture.

Method C

Reaction of the compound of the formula

[Structure VI: 3-CF₃-phenyl-NH—CH₂—CH₂—NH—CH₂—C≡CH]   (VI)

with a compound of the formula

X—CH₂—CH₂—X   (VII)

in which X has the above-mentioned meanings, at temperatures between room temperature and the boiling point of the reaction mixture.

Method D

Introduction of the propargyl group into the compound N-(3-trifluoromethylphenyl)-piperazine by means of conventional propargylation methods, such as, for example, reaction with a compound of the formula

HC≡C—CH₂—X   (VIII)

in which X has the above-mentioned meaning at temperatures between room temperature and the boiling point of the reaction mixture.

Method E

Reduction of the dione of the formula

[Structure IX: 3-CH₃-phenyl-N(piperazine-2,6-dione)N—CH₂—C≡CH]   (IX)

with a reducing hydride at temperature between about 0° C. and the boiling point of the reaction mixture.

Method F

Reduction of the dione of the formula

[Structure X: 3-CF₃-phenyl-N(piperazine-2,6-dione)N—CH₂—C≡CH]   (X)

with a reducing hydride at temperatures between about 0° C. and the boiling point of the reaction mixture.

Method G

Reduction of the dione of the formula

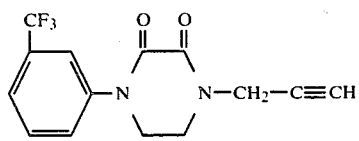 (XI)

with a reducing hydride at temperatures of about 0° C. and the boiling point of the reaction mixture.

The above reactions are carried out in known manner.

A solvent which is inert under the reaction conditions is advantageously used as a reaction medium, for example for methods A and B a lower aliphatic alcohol such as butanol, and for method C, for example, toluene. For method D acetonitrile has proved to be appropriate as a solvent, while for methods E, F and G ethers, for example diethylether or tetrahydrofuran in particular, can be used.

If an acid is released during the reactions, additions can be made to bind the acid. For this purpose, for example, sodium bicarbonate or sodium carbonate (methods A, B and D), or organic bases, for example triethylamine (especially in method C), come under consideration.

Hydrides, such as lithium aluminum hydride or boron hydride, are suitable as reducing agents for methods E, F and G.

The starting compounds of the formulas II and XI are either already known or can easily be prepared according to conventional methods. Reference is made in this respect to the methods described in more detail in German Pat. No. 2,442,158.

The starting compound N-(3-trifluoromethyl-phenyl)-piperazine used for method D can be prepared by the method described in Irish Pat. No. 28,880.

The starting materials for methods E to G can be prepared according to the following diagramatic reaction sequences:

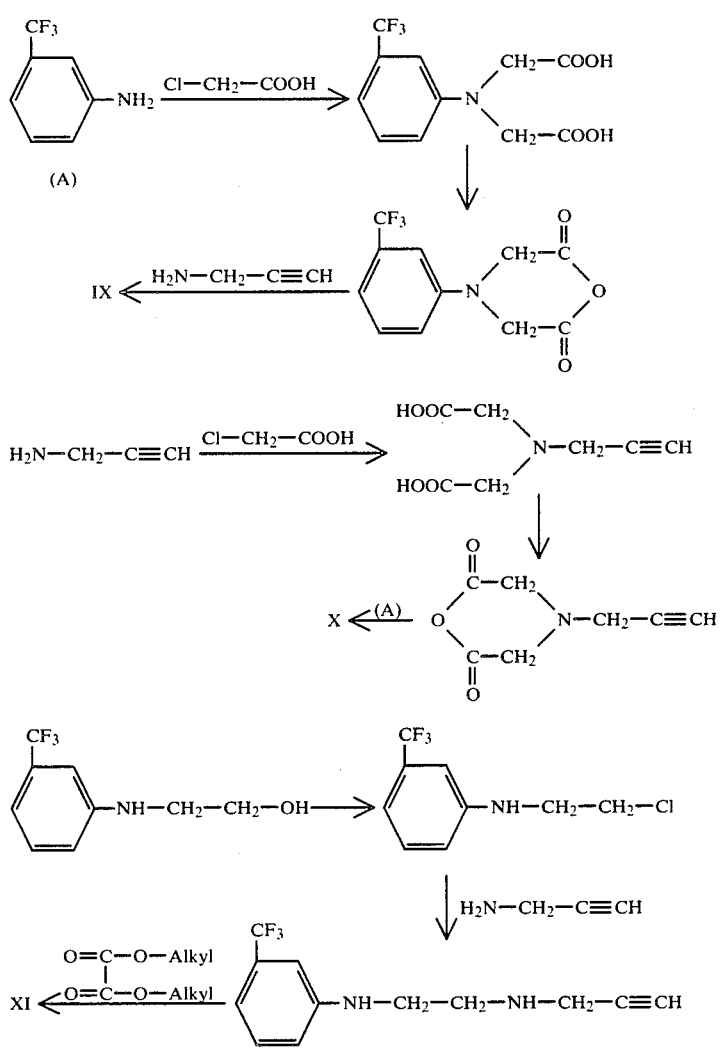

The compound of the present invention is basic and therefore forms addition salts with inorganic or organic acids or acid synthetic resins. Examples of non-toxic, pharmacologically acceptable acid addition salts are those formed with hydrochloric acid, hydrobromic acid, phosphoric acid, sulfuric acid, methanesulfonic acid, maleic acid, acetic acid, oxalic acid, lactic acid, tartaric acid, 8-chloro-theophylline, salicylic acid, citric acid, β-naphthoic acid, adipic acid, 1,1-methylene-bis- (2-hydroxy-3-naphthoic acid), a sulfonated polystyrene resin or the like.

The following examples illustrate the present invention and will enable others skilled in the art to understand it more completely. It should be understood, however, that the invention is not limited solely to the particular examples given below.

EXAMPLE 1

N-(3-Trifluoromethyl-phenyl)-N'-propargyl-piperazine hydrochloride by method A 16.5 g (0.3 mol) of propargylamine were added gradually dropwise at room temperature to 28.6 g (0.1 mol) of N,N-bis-(2-chloro-ethyl)-3-trifluoromethyl-aniline in n-butanol, and the reaction was caused to go to completion by heating to 100° C., while monitoring its progress by chromatography. After the reaction had gone to completion the n-butanol was distilled off under reduced pressure.

The distillation residue was made alkaline in water with the equivalent quantity of sodium carbonate. The N-propargyl-N'-(3-trifluoromethyl-phenyl)-piperazine was extracted with ether. After drying the organic solution with sodium sulfate, the ether was evaporated under reduced pressure, and the base was reacted conventionally to form the hydrochloride, using a stoichiometric quantity of hydrogen chloride. Even small quantities of dihydrochloride influence the melting point.

White crystals from acetonitrile, melting point 218°–219° C. (decomposition).

This reaction can be carried out analogously with N,N-bis-(2-methysulfonyloxyethyl)-3-(trifluoromethyl)-aniline, prepared according to M. P. Mertes et al., J. Med. Chem. 12 (5), 825–28 (1969).

Example 2

N-(3-Trifluoromethyl-phenyl)-N'-propargyl-pierazine hydrochloride by method B

A mixture of 16.1 g (0.1 mol) of 3-(trifluoromethyl)-aniline and 21.6 g (0.1 mol) of N,N-bis-(2-chloro-ethyl)-N-propargyl-amine hydrochloride in 150 ml of n-butanol was refluxed. The acid reaction occurring during the reaction was buffered by means of sodium bicarbonate. The water released at the same time was removed azeotropically. The reaction, monitored by means of chromatography, sometimes required an excess of 3-trifluoromethyl-aniline.

After the reaction had gone to completion, the resulting suspension was cooled to 10° C., and the solid product was collected by suction filtration. The n-butanol was distilled off under reduced pressure, and the collected product and the distillation residue were dissolved in water, the solution was extracted several times with ether. The aqueous phase was made alkaline with the equivalent quantity of sodium carbonate, and the reaction product was extracted with ether. After drying with sodium sulfate, the ethereal solution was evaporated under reduction pressured, and the residual base was reacted conventionally with the stoichiometric quantity of hydrogen chloride to form the hydrochloride.

White crystals from acetonitrile, melting point 218°–219° C. (decompositon).

EXAMPLE 3

N-(3-Trifluoromethyl-phenyl)-N'-propargyl-piperazine hydrochloride by method C 3.1. N-(2-Chloro-ethyl)-3-trifluoromethyl-aniline hydrochoride 20.5 g (0.1 mole of N-(2-hydroxy-ethyl)-3-trifluoromethyl-aniline were taken up in 100 ml of absolute methylene chloride, and the solution was cooled to 0° C. At this temperature 14.3 g (0.12 mol) of thionyl chloride were added dropwise. The reaction mixture was allowed to warm to room temperature while stirring, whereupon it was refluxed, while monitoring by chromatography, until the reaction had gone to completion. After the solvent and the residual thionyl chloride had been removed, the crude product thus obtained was used for further reaction.

3.2. N-Propargyl-N'-(3-trifluoromethyl-phenyl)-ethylene diamine 16.5 g of (0.3 mol) of propargylamine were dissolved in 100 ml of absolute methylene chloride, and the solution was admixed at room temperature in portions with the N-(2-chloro-ethyl)-3-(trifluoromethyl)-aniline hydrochloride obtained in step 3.1. While monitoring by chromatography, the mixture was heated until the reaction had gone to completion. After the reaction had ended, the reaction solution were extracted with the calculated quantity of sodium carbonate solution. After drying with sodium sulfate, the organic phase was evaporated under reduced pressure. The oily base thus obtained was used as such in the next step. (If this product contains significant impurities, it is advisable to recrystallize as its dihydrochloride).

3.3. N-Propargyl-N'-(3-trifluoromethyl-phenyl)-piperazine hydrochloride

A mixture consisting of the N-propargyl-N'-(3-trifluoromethylphenyl)-ethylene diamine obtained in step 3.2. and 20.2 g (0.2 mol) of triethylamine was heated at 100° C. in 500 ml of absolute toluene, while 18.8 g (0.1 mol) of dibromoethane were added dropwise. The mixture was heated until the reaction had gone to completion, as indicated by chromatographic monitoring. After the reaction had ended, the reaction solution was extracted with the calculated quantity of sodium carbonate solution. After drying with sodium sulfate, the organic phase was evaporated under reduced pressure, and the residual base was converted into its hydrochloride with a stoichiometric quantity of hydrogen.

White crystals from acetonitrile, melting point 218°–219° C. (decomposition).

EXAMPLE 4

N-(3-Trifluoromethyl-phenyl)-N'-propargyl-piperazine hydrochloride by method D 4.1. N-(3-Trifluoromethyl-phenyl)-piperazine hydrochloride 71.4 g (0.4 mol) of bis-(2-chloro-ethyl)-amine hydrochloride and 64.4 g (0.4 mol) of 3-trifluoromethyl-aniline were suspended in 500 ml of n-butanol, and the suspension was refluxed. The acid reaction was buffered with sodium bicarbonate. The water released at the same time was removed azeotropically. This procedure was repeated twice, each time after an interval of 24 hours, and each time with 12.9 g (0.08 mol) of 3-trifluoromethyl-aniline. After the reaction had ended, the suspension was cooled to 10° C. and the crystals were collected by suction filtration. The n-butanol was distilled out of the filtrate under reduced pressure. The collected crystals and the distillation residue were dissolved in water, and the solution was extracted several times with ether. The aqueous phase was made alkaline with sodium carbonate and extracted thoroughly with ether. After drying with sodium sulfate, the organic phase was evaporated under reduced pressure, and the residual base was converted into the hydrochloride in conventional manner.

White crystals from ethanol. Melting point 236°-237° C. (decomposition).

Yield: 65.2 g (61.1% of theory).

4.2.
N-(3-Trifluoromethyl-phenyl)-N'-propargyl-piperazine hydrochloride 3.2 g (0.012 mol) of N-(3-trifluoromethyl-phenyl)-piperazine hydrochloride, 0.9 g (0.012 mol) of propargyl chloride and 2.5 g (0.024 mol) of sodium carbonate were heated at 60° C. in 50 ml of absolute acetonitrile while stirring. Over a period of 15 hours, an additional 0.34 g (0.0046 mol) of propargyl chloride and 0.5 g (0.0046 mol) of sodium carbonate were added. The inorganic salts were removed by suction filtration, and the filtrate was evaporated under reduced pressure. The evaporation residue was dissolved in toluene, and the product solution was extracted with the calculated quantity of dilute hydrochloric acid. The aqueous phase was made alkaline with soda, and the base was extracted with ether. After drying with sodium sulfate, the organice phase was evaporated under reduced pressure, and the base was converted into its hydrochloride in conventional manner. White crystals from acetonitrile, melting point 218°-219° C. (decomposition). Yield: 2.7 g (73.8% of theory). The existence of these compounds was confirmed by elemental and spectrum analysis.

EXAMPLE 5

N-(3-Trifluoromethyl-phenyl)-N'-propargyl-piperazine hydrochloride by method E 5.1. 3-(Trifluoromethyl-phenyl)-iminodiacetic acid The 3-(trifluoromethylphenyl)-iminodiacetic acid was prepared from 3-trifluoromethyl-aniline analogous to A. Reissert, Ber. Dtsch. Chem. Ges. 57, 993 (1924), or N. B. Tien, J. Org. Chem. 23, 186 (1958).

5.2.
1-Propargyl-4-(3-trifluoromethyl-phenyl)-piperazin-2,6,-dione

The compound obtained in step 5.1. was converted into the acid anhydride and was then reacted with propargylamine to form 1-propargyl-4-(3-trifluoromethyl-phenyl)-piperazin-2,6-dione.

5.3. Reduction to form the end product

The dione obtained in step 5.2. was reduced to the desired end product at reflux temperature with borane/-tetrahydrofuran or lithium aluminum hydride in ether (analogous to D. W. Henry, J. Het. Chem. 3, 503 (1966), or G. Cignarella, J. Med. Chem. 7, 242 (1964). The hydrochloride was obtained in analogy to Example 1; melting point 218°-219° C. (decomposition).

EXAMPLE 6

N-(3-Trifluoromethyl-phenyl)-N'-propargyl-piperazine hydrochloride by method F 6.1. Propargyliminodiacetic acid anhydride Propargylaminodiacetic acid was first prepared from propargylamine with chloroacetic acid and was then converted into the anhydride.

6.2.
4-Propargyl-1-(trifluoromethylphenyl)-piperazin-2,6-dione

Reaction of the acid anhydride obtained in step 6.1 with 3-trifluoromethyl-aniline gave the dione mentioned above.

6.3. Reduction to form the end product

The dione obtained in step 6.2. was reduced at a temperature up to the reflux temperature with borane/tetrahydrofuran or lithium aluminum hydride. The mode of operation corresponded to that of Example 5. Melting point 218°-219° C. (decomposition).

EXAMPLE 7

N-(3-Trifluoromethyl-phenyl-N'-propargyl-piperazine hydrochloride by method G

Condensation of N-propargyl-N'-(3-trifluoromethyl-phenyl)-ethylenediamine, obtainable according to 3.2, with diethyloxalate gave 1-propargyl-4-(3-trifluoromethyl-phenyl)-piperazin-2,3-dione. This compound was reduced to the title compound with lithium aluminum hydride or borane and was processed according to Example 5. White crystals, melting point 218°-219° C. (decomposition).

Instead of with HCl, the free base can also be converted into the corresponding salts, for example, with HBr, $H_2SO_4$, $HNO_3$, $CH_3COOH$ or other acids.

The compounds of the present invention, that is, N-(3-trifluoromethyl-phenyl)-N'-propargyl-piperazine and its non-toxic, pharmacologically acceptable acid addition salts. have useful pharmacologic properties. More particularly, they exhibit analgesic activity in warm-blooded animals such as rats and rabbits.

In comparison with known analgesic substances, such as, for example, metamizol sodium, they are characterized by a substantial lack of side effects. It can be concluded from the pharmacological experiments carried out that these are a new type of analgesic compound.

The pharmacological data given below show the useful properties of N-(3-trifluoromethyl-phenyl)-N'-propargyl-piperazine hydrochloride according to the invention in comparison with the known analgesic metamizol (Novalgin ®).

| Compound | Writhing test $ED_{50}$ s.c./p.o. (mg/kg) | Gait test (s.c.) $ED_{50}$ (mg/kg) | Rabbit's tooth pulp test (s.c.) $ED_{IV}$ |
|---|---|---|---|
| A. Invention | | | |
| N—(3-trifluoromethyl-phenyl)-N'—propargyl-piperazine hydrochloride | 5.3/43 | 2.8 | approx. 10 |
| B. Comparison | | | |
| Metamizole-sodium | 25/80 | 97 | approx. 560 |

-continued

| Compound | Writhing test ED$_{50}$ s.c./p.o. (mg/kg) | Gait test (s.c.) ED$_{50}$ (mg/kg) | Rabbit's tooth pulp test (s.c.) ED$_{IV}$ |
|---|---|---|---|
| (Novalgin ®) | | | |

Literature

1. Writhing test
   Linne, Ph., J. Pharmacol. (Paris) 3,4, p. 513–515 (1972)
2. Gait test
   Atkinson, D. C., and Cowan, A. J., Pharm. Pharmacol. 26, 727–728 (1974)
3. Rabbit's tooth pulp test
   Hoffmeister, F., Arzneimittelf. 16 (supplement), 1968.

For pharmaceutical purposes the compounds of the present invention are administered to warm-blooded animals perorally or parenterally as active ingredients in customary pharmaceutical compositions, that is, compositions consisting essentially of an inert pharmaceutical carrier and an effective amount of the active ingredient.

An effective amount of the substances according to the invention is around 50 to 500 mg, preferably 75 to 200 mg orally), or 15 to 150 mg, preferably 25 to 75 mg (parenterally).

The active substances according to the invention can be formulated in the conventional galenic forms of administration, such as tablets, coated tablets, solutions, emulsions, powders, capsules or sustained release forms, and the conventional pharmaceutical excipients and the conventional production methods can be adopted for preparing them. Appropriate tablets can be obtained, for example, by mixing the active substance with known excipients, for example inert diluents, such as calcium carbonate, calcium phosphate or lactose, disintegrating agents, such as corn starch or alginic acid, binders, such as starch or gelatin, lubricants, such as magnesium stearate or talc, and/or agents for obtaining a sustained release effect, such as carboxypolymethylene, carboxymethylcellulose, cellulose, acetatephthalate or polyvinylacetate.

The tablets can also consist of several layers. Accordingly, coated tablets can be prepared by convering cores, produced in a similar way to the tablets, with agents used conventionally in coated-tablet coverings, for example polyvinylpyrrolidone or shellack, gum arabic, talc, titanium dioxide or sugar. To achieve a sustained release effect or to prevent incompatibilities, the core can also consist of several layers. Likewise, the coated-tablet envelope can also consist of several layers to achieve sustained release effect, and the excipients mentioned above in connection with the tablets can be used.

Juices of the active substances or active-substance combinations according to the invention can additionally also contain a sweetening agent, such as saccharin, cyclamate, glycerol or sugar, and a flavor-improving agent, for example aromatics, such as vanillin or orange extract.

They can contain, moreover, suspension auxiliaries or thickeners, such as sodium carboxymethylcellulose, wetting agents, for example condensation products of fatty alcohols with ethylene oxide, or protective substances, such as p-hydroxybenzoates.

Injection solutions are prepared in a conventional way, for example with the addition of preservatives, such as p-hydroxybenzoates, or stabilizers, such as complexones, and are filled in injection bottles or ampules.

Capsules containing the active substances or active-substance combinations can be prepared, for example, by mixing the active substances with inert carriers, such as lactose or sorbitol, and encapsulating them in gelatin capsules.

Suitable suppositories can be prepared, for example, by mixing the appropriate active substances or active-substance combinations with conventional carriers, such as neutral fats or polyethylene glycol or its derivatives. The substances according to the invention are also suitable for combination with other pharmacodynamically active substances, such as, for example, tranquilizers.

The following examples illustrate a few pharmaceutical compositions comprising a compound of the present invention as an active ingredient and represent the best modes contemplated of using the invention. The parts are parts by weight unless otherwise specified.

EXAMPLE 8

TABLETS

The tablet compositon is compounded from the following ingredients:

| | |
|---|---|
| N—(3-trifluoromethyl-phenyl)-N"—propargyl piperazine hydrochloride | 75.0 parts |
| Corn starch | 164.0 parts |
| Secondary calcium phosphate | 240.0 parts |
| Magnesium stearate | 1.0 parts |
| Total | 480.0 parts |

Preparation

The individual ingredients are mixed intensively with one another, and the mixture is granulated in conventional manner. The granulate is compressed into tablets weighing 480 mg, each of which contains 75 mg of active substance.

EXAMPLE 9

Gelatin capsules

The capsule filler composition is compounded from the following ingredients:

| | |
|---|---|
| N—(3-trifluoromethyl-phenyl)-N"—propargyl-piperazine hydrochloride | 50.0 parts |
| Corn starch | 200.0 parts |
| Total | 250.0 parts |

Preparation

The ingredients are mixed intensively, and 250 mg-portions of the mixture are filled into gelatin capsules of suitable size. Each capsule contains 50 mg of active substance.

EXAMPLE 10

Coated sustained release tablets

The tablet core composition is compounded from the following ingredients:

| | |
|---|---|
| N—(3-trifluoromethyl-phenyl)-N'—propargyl-piperazine hydrochloride | 60.0 parts |
| Carboxymethylcellulose (CMC) | 295.0 parts |
| Stearic acid | 45.0 parts |
| Cellulose acetate phthalate (CAP) | 40.0 parts |
| Total | 440.0 parts |

Preparation

The active substance, the CMC and the stearic acid are mixed intensively, and the mixture is granulated in conventional manner, using a solution of CAP in 200 ml of a mixture of ethanol and ether acetate. The granulate is then compressed into 400 mg-tablet cores which are subsequently covered conventionally with a sugar-containing 5% solution of polyvinylpyrrolidone in water. Each coated tablet contains 60 mg of active substance.

EXAMPLE 11

Tablets

The tablet composition is compounded from the following ingredients.

| | |
|---|---|
| N—(3-trifluoromethyl-phenyl)-N'—propargyl-piperazine hydrochloride | 75.0 parts |
| Diazepam | 10.0 parts |
| Lactose | 164.0 parts |
| Corn starch | 194.0 parts |
| Colloidal silicic acid | 14.0 parts |
| Polyvinylpyrrolidone | 6.0 parts |
| Magnesium stearate | 2.0 parts |
| Soluble starch | 10 parts |
| Total | 475.0 parts |

Preparation

The active substance is granulated conventionally, together with the lactose, corn starch, colloidal silicic acid and polyvinylpyrrolidone, after intensive mixing, an aqueous solution of the soluble starch being used. The granulate is mixed with the magnesium stearate and compressed into tablets, each weighing 475 mg and containing 75 mg of the first active substance and 10.0 mg of the second.

The free base or any one of the other non-toxic, pharmacologically acceptable acid addition salts thereof may be substituted for the hydrochloride in Examples 8 through 11. Likewise the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. The compound of the formula

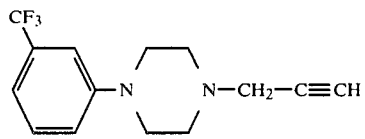

or a non-toxic, pharmacologically acceptable acid addition salt thereof.

2. The compound of claim 1, which is N-(3-trifluoromethyl-phenyl)-N'-propargyl-piperazine hydrochloride.

3. An analgesic pharmaceutical composition consisting essentially of an inert pharmaceutical carrier and an effective analgesic amount of a compound of claim 1.

4. The method of raising the pain threshold of a warmblooded animal in need thereof, which comprises perorally or parenterally administering to said animal an effective analgesic amount of a compound of claim 1.

* * * * *

UNITED STATES PATENT AND TRADEMARK OFFICE
CERTIFICATE OF CORRECTION

PATENT NO. : 4,699,910

DATED : October 13, 1987

INVENTOR(S) : ROLF BANHOLZER ET AL.

It is certified that error appears in the above-identified patent and that said Letters Patent is hereby corrected as shown below:

Column 5, line 62: "reduction pressured" should read -- reduced pressure --.

Column 9, line 48: "convering" should read -- covering --.

Column 10, lines 31 and 51: "N"-propargyl" should read -- N'-propargyl --.

Signed and Sealed this

Seventeenth Day of May, 1988

Attest:

DONALD J. QUIGG

*Attesting Officer*  *Commissioner of Patents and Trademarks*